United States Patent [19]

Wayland et al.

[11] Patent Number: 4,891,969
[45] Date of Patent: Jan. 9, 1990

[54] OIL/WATER RATIO MEASUREMENT

[76] Inventors: J. Robert Wayland, 580 Oakwood Pl., N. E., Albuquerque, N. Mex. 07123; Caroline H. Persson-Reeves, 1013 Lynch Ct. N. W., Albuquerque, N. Mex. 87104

[21] Appl. No.: 216,073
[22] Filed: Jul. 7, 1988
[51] Int. Cl.$^4$ .......... G01N 25/58; G01F 5/00
[52] U.S. Cl. ................................. 73/61.1 R
[58] Field of Search ............ 73/61.1 R, 61 R, 861.03, 73/861.04

[56] References Cited

U.S. PATENT DOCUMENTS

| | | | |
|---|---|---|---|
| 2,807,956 | 10/1957 | Doble | 73/61.1 R |
| 3,049,910 | 8/1962 | Topol | 73/61.1 R |
| 3,238,452 | 3/1966 | Schmitt et al. | 324/61 R |
| 3,264,558 | 5/1963 | Heeps | 324/65 P |
| 3,304,766 | 2/1967 | Hubby | 73/61.1 R |
| 3,349,304 | 8/1969 | Brenchley | 318/118 |
| 3,387,748 | 6/1966 | Brenchley | 222/644 |
| 3,430,489 | 3/1969 | Pfrehm | 73/861.03 |
| 3,522,530 | 8/1970 | Muller | 324/65 R |
| 3,580,072 | 5/1971 | Cox et al. | 73/861.03 |
| 3,693,435 | 9/1972 | Cox et al. | 73/861.04 |
| 3,961,530 | 6/1976 | Helgesson | 374/162 |
| 4,059,987 | 11/1977 | Dowling | 73/61.1 R |
| 4,080,837 | 3/1978 | Alexander et al. | 73/61.1 R |
| 4,166,216 | 8/1979 | Cubberly | 250/260 |
| 4,190,768 | 2/1980 | Arnold et al. | 376/159 |
| 4,200,789 | 4/1980 | Arnold et al. | 376/159 |
| 4,215,567 | 8/1980 | Vlcek | 73/61.1 R |
| 4,236,406 | 12/1980 | Reed et al. | 73/61.1 R |
| 4,644,263 | 2/1987 | Johnson | 324/65 P |
| 4,773,257 | 9/1988 | Aslesen et al. | 73/61.1 R |

FOREIGN PATENT DOCUMENTS

| | | | |
|---|---|---|---|
| 255914 | 4/1970 | U.S.S.R. | 73/61.1 R |
| 1196742 | 12/1985 | U.S.S.R. | 73/61.1 R |
| 2170909 | 8/1986 | United Kingdom | 73/61.1 R |

Primary Examiner—John Chapman
Assistant Examiner—Joseph W. Roskos
Attorney, Agent, or Firm—Richards, Medlock & Andrews

[57] ABSTRACT

A method and apparatus for the determination of the ratio of components in a multicomponent liquid mixture such as oil and water. The apparatus including a conduit for flow of fluid, a first temperature sensing thermocouple, a plurality of plates disposed in said conduit to uniformly mix the liquid, a microwave energy generator, a second temperature sensing thermocouple downstream of the microwave generator and a flow measuring meter.

25 Claims, 3 Drawing Sheets

OIL/WATER RATIO MEASUREMENT

TECHNICAL FIELD

The invention relates to a measuring device, and in particular a device for determining the ratio of components having different electrical properties in a mixture of those components. The invention is particularly useful in determining the ratio of oil and water present in oil-field operations.

BACKGROUND OF THE INVENTION

The present invention relates to an empirical two-step technique for sensing the oil/water ratio (cut) utilizing a small unit that is in-line in a fluid transport piping system or in a bypass mode outside the main transport system.

Water occurs naturally in hydrocarbon formations and is used in the secondary recovery of oil from wells. Because of the increased value of crude oil extracted with a lower content of water, it is important to maintain the highest possible oil/water ratio. Without timely measurements of the oil/water cut at the wellhead, effective production activities are difficult to ascertain. Therefore, the measurement of the oil/water cut is important to the efficient recovery of oil.

Historically, oil/water cut measurements have relied upon taking samples, separating the oil and water, and measuring the volumes of the separated components. This can be done at individual wells by taking samples at a wellhead or at a block of wells by measuring the water in the separating tank.

It has been proposed to measure the water content in an oil/water mixture by measuring the electrical properties of the mixture. By far, the majority of the techniques measure capacitance rather than resistance. The primary difference with each technique lies within the specific electrical properties which are being measured; the overall methodologies and apparatus are similar (often identical) and similar problems with accuracy arise, as will be discussed below.

One technique is to pass the oil/water mixture between two parallel plates (test cell). Using the test cell, the dielectric constant of the oil/water mixture is determined by measuring the dielectric capacity. Using the same test cell, one could measure the resistance (or conductance) of the mixture. This technique is inaccurate because the electrical measurement requires an unusually accurate knowledge of the physical dimensions of the test cell which must remain fixed when used in the field if recalibration of the device is to be avoided.

For capacitance measurements, the change in capacitance with water content, particularly at low ambient temperatures, is so small that the sensitivity of the measurement is inadequate. This problem has been addressed by placing a water-sorptive, solid dielectric material in contact with the fluid and determining its electrical loss characteristics. Because any practical water-sorptive material displays an hysteresis with changing water content, again, continuous recalibration is necessary, severely limiting the usefulness of this device.

An extension of these techniques is one in which a grid pattern of crossed vertical and horizontal wires is used to determine the location of clusters of conductive water in a nonconductive fluid, thus implying the water content. The spacing of the wires determines the spatial resolution. For a heterogeneous mixture of oil and water, there is a problem in establishing the water content.

These techniques are most accurate in the middle range. When either oil or water dominate the mixture, the sensitivity of these measurements decreases dramatically. However, for end member ratios, capacitance measurements are more accurate than measurements of resistance.

Non-electrical methods depend upon differences of physical properties. Those methods utilizing the differences in physical properties usually require taking a sample and allowing the oil and water to separate. Although accurate, they are essentially an extension of techniques that have been in use for many years and suffer from the limitations mentioned below.

Another method depends upon measuring gamma rays resulting from capture of thermal neutrons. For the gamma/neutron techniques, the fluid is bombarded with fast neutrons which become thermalized and are then captured by materials in the fluid mixture; these materials then emit high energy gamma rays. The intensity and spectra of the gamma rays allow one to estimate the oil/water cut. Differences in neutron absorption are induced by the varying composition of the oil/water mixture. Periodic certification and great care in handling the neutron source are required. This technique is variable and very expensive.

One unusual technique measures sonic velocities of a flowing oil/water mixture from which the oil/water cut may be determined. As with the electrical techniques, this technique requires careful attention to the influence of environmental parameters such as ambient and oil/water temperatures.

In all of these methods, the information is not timely. In those where measurements are made at a separating tank, only a gross indication of where the problem actually exists is given. Thus, a method is needed that can sense the oil/water cut at the wellhead or at another location within the pipeline that is accurate and can be measured within whatever time frame is desired. A method which allows remote readings will enhance the overall economy and usefulness of the technique. The output from such a device should be easily and immediately transmittable to a convenient location. This would allow one to quickly assimilate an accurate picture of the state of a project.

SUMMARY OF THE INVENTION

In the above and following paragraphs, the use of the term "oil/water" implies that the considerations will apply to any two-component fluid mixture in which there is a large difference in physical properties. For this invention, the technique will work and is applied to multi-component liquids, or mixtures of two or more liquids, in which there is a difference in the electrical and thermomechanical properties of the components. The method and apparatus of the present invention will also be useful in determining the ratio of components in a mixture of miscible liquids or combinations of miscible and immiscible liquids.

Accordingly, one aspect of the present invention is to provide an empirical method for the sensing of the oil/water cut.

Another aspect of the present invention is to provide an empirical method for sensing the oil/water cut that can be easily adapted for remote oil/water cut measurements.

Another aspect of the present invention is to provide a device for allowing measurement of the mixture of oil and water which will not alter the flow characteristics and, at the same time, be able to withstand an adverse environment.

Yet another aspect of the present invention is to provide a device whose sensing signal can be instantaneously read, and/or be hardwired to a central processing station, and/or is capable of being sent back via a telemetering link.

More specifically, the present invention is directed to a method for measuring the oil/water cut of a multi-component liquid flowing through a conduit. The invention is a method comprising the steps of: (a) uniformly mixing an oil/water sample; (b) applying a microwave field (MWF) of a selected frequency to the multi-component liquid; (c) measuring the temperature increase produced by the application of the MWF; and (d) determining the oil/water cut from said temperature increase. In the preferred embodiment the method includes the additional steps of monitoring the temperature change of the liquid mixture, and increasing or decreasing the amount of MWF applied to the liquid mixture to produce a temperature change which is more easily measured.

The invention also relates to an apparatus useful in practicing the method of the invention comprising: a conduit defining passageway for the flow of a liquid mixture; means for measuring the flow of liquid within the conduit; mixing means located in the conduit for mixing the liquid within the conduit to achieve a uniform mixing; means for applying a microwave field to the liquid mixing; means to measure the temperature of the liquid mixture prior to application of the microwave field and means to measure the temperature of the liquid mixture after application of the microwave field; and means to determine the ratio of components in the liquid mixture from said measurements; and means to determine the flow rate.

Further scope of applicability of the present invention will become apparent from the detailed description given below. However, it should be understood that the detailed description and specific examples, while indicating preferred embodiments of the invention, are given by way of illustration only, since various changes and modifications within the spirit and scope of the invention will become apparent from the detailed discussion to those skilled in the art.

BRIEF DESCRIPTION OF THE DRAWINGS

The present invention will become fully understood from the detailed description given below and the accompanying drawings which are given by way of illustration only, and thus are not limitations of the present invention and wherein.

DETAILED DESCRIPTION

Briefly described, in accordance with the present invention, an electro-thermal-mechanical method for sensing of the oil/water cut for a flowing mixture of liquids has been developed. A device is made using a two-step technique that requires the temporary or permanent installation of a measuring unit. This unit may be installed either in-line or in a bypass mode that does not interfere with the fluid flows. For safety, it is preferred that the device is electrically insulated from the earth and/or the inlet and outlet connections to the conduit (described below). This device is calibrated on a site-specific basis. Clearly, this technique can be adapted to other applications.

The MWF may be either applied externally to the flowing sample through a nonconductive conduit or directly into a conductive conduit acting as a waveguide, or by any other available technique.

In any case, the devices are installed in a pipe (conduit) where a measurement of the oil/water cut is desired. The measurement can be electronically transmitted to any desired processing station. As part of the calibration procedure, it is important to verify exigencies of production activities, accounting information, proper maintenance, and corrective actions.

Figure 1:
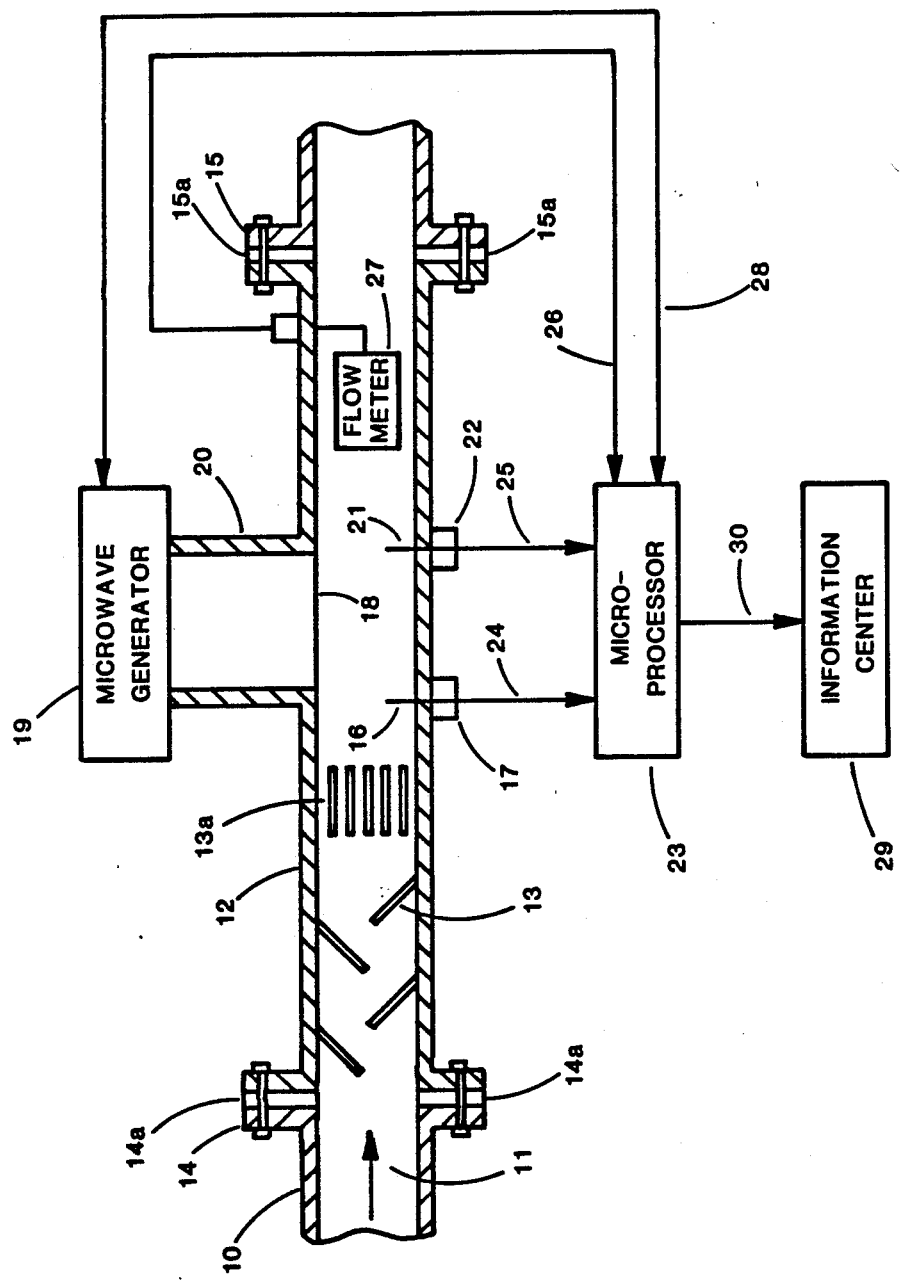
FIG. 1 is a diagrammatic view illustrating the mixing means, the microwave application equipment, and the temperature and liquid-flow measurement equipment.

FIG. 1 illustrates a conduit 10 which is suitable for a mixture of crude oil and water 11 as may be found at an oil well production site. The oil/water cut is usually known with little accuracy. One embodiment of the measuring apparatus shown generally as conduit section 12, which is a wall defining a passageway therethrough, which includes a mixing means 13 for uniformly mixing the fluid, is placed in-line with the fluid flow. The measuring apparatus can be attached inline by flanges 14 and 15. The apparatus can be electrically and thermally insulated from the pipes by insulating gaskets 14a and 15a, which can be made of any suitable insulating material such as Teflon.

The mixing means 13 can be any of a number of commercially available devices. Normally, this element consists of a plurality of plates, as shown, which form a plurality of tortuous flow routes selected to provide shear and a uniform mixture of fine droplet size in the output oil/water mixture. The water and oil are not miscible, and droplets of the phase in the minor concentration will be uniformly dispersed throughout the larger volume fluid. The mixing means usually includes an assembly of straightening vanes 13a to reduce flow disturbances before entry into the next phase of the metering conduit section 12. The straightening vanes can be of any design known in the art.

Just after the mixing means 13, a first temperature measuring means 16 is inserted in-line through port 17 for measuring temperature. The first temperature measuring means 16 may be a thermocouple, thermistor, or any other suitable temperature sensing apparatus. Downstream of the first temperature measuring means for is the MWF energy means for providing MWF energy which is illustrated as MWF generator 19, waveguide 20 and window 18. The MWF energy means can be commercially available, such as the type used in microwave ovens. A number of frequencies are available and can be used, such as 250 MHz. The window 18 is composed of a material that is transparent to microwave energy, such as glass. The energy from the microwave generator 19 is guided by the waveguide 20 through window 18 into the oil/water mixture and will heat the mixture.

The window 18, the microwave generator 19, the waveguide 20, and the conduit 10 is dimensioned in accordance with standard microwave engineering principles. The dimensions of the microwave generator will be determined by the electromagnetics of the MWF in accordance with the relationship between the microwave frequency and Maxwell's equations. The source will also be dimensioned to most efficiently heat the oil/water mixture to a uniform temperature or in such a manner as to provide the most accurate measurement of the oil/water cut. This design will be such that maximum heating efficiency is achieved without allowing the mixture to become nonuniform. Downstream of the MWF energy means is a second measuring means 21, mounted through port 22. Measuring means 21 may be a thermocouple, thermometer or other suitable temperature sensing apparatus. In the embodiment illustrated, a flow measuring means 27 is provided. Flow measuring means 27 may be any one of the generally available commercial flow meters, such as a sonic flow meter or a rotating valve flow meter. While the flow measuring means is illustrated positioned downstream of the MWF generator it can be located at any suitable location upstream or downstream of the MWF generator.

The first and second measuring means 16 and 21 are connected by suitable leads to microprocessor 23; flow meter 27 and microwave generator 19 can be connected to the microprocessor by leads 26 and 28 to provide an automated system. Of course, it is recognized that measurement of flow rate, temperature, and operation of the microwave generator may be manually controlled or controlled by other means than a microprocessor. The microprocessor 23 reads and stores flow rate, microwave generator power level, the temperatures (from the temperature measuring means), and other relevant environmental parameters. The microprocessor 23 is programmed such that it will control the operation of the microwave generator to provide the correct amount of energy needed to produce an accurately measurable temperature increase. Also, the microprocessor will contain the equation, material properties (determined from the calibration procedures described below) and response functions (perhaps in tabular form) required to provide the oil/water cut measurement. This information is then stored in the microprocessor for retrieval, either manually or by a remote telemetering link. The microprocessor will also control the linking to the central information center.

In a method of the present invention, the liquid to be measured can consist of total flow in a pipeline or conduit, for example, from a well head, or can consist of a fraction forced to flow in a bypass pipeline or conduit. The oil and water mixture is first mixed to provide a uniform mixture. In the case of oil and water this would result in a emulsion. The invention is being described in its preferred embodiment, which in the oil industry are usually immiscible fluids. However, this invention will also work for miscible fluids, in this specific case, only a minimum mixing may be required, or no mixing at all. Thus, for some applications the mixing means need not be part of the device. After the mixing step, the temperature of the uniform mixture is measured by a suitable temperature sensor, thereafter the mixture is heated by microwave energy, followed by the measurement of the temperature of the mixture after it has been heated by microwave energy. The final step of the process is to determine the temperature difference to determine the ratio of components. From Equation 3, described below, it is shown that the temperature differential is directly proportional to the power level of the MWF and inversely proportional to the velocity of the oil/water mixture. Thus, when the power level of the microwave generator is increased (or decreased), the temperature differential will be increased (or decreased). The power level of the microwave generator must be measured if one is to correlate temperature to the oil/water ratio.

When the velocity of the fluid is increased (or decreased), the temperature differential is decreased (or increased). Thus, the inverse relationship of the temperature increase to fluid velocity requires knowledge of the fluid velocity. As shown by the relationship between Equations 3 and 5, the temperature differential ($\Delta T$) is a function of the power level and time. Therefore, the flow rate ($v$) is necessary to determine the time ($\Delta t$) the mixture remains in the MWF. In the preferred embodiment, the invention also relates to monitoring the temperature before and after heating, determining whether the change in temperature is too high or too low for successful measurement of ratios and increasing or decreasing the energy input as desired. The process of the present invention is described in further detail with respect to the operation of the preferred apparatus.

The window 18 keeps fluid out of the waveguide 20. The fluid is heated as described above. The temperature of the heated fluid is measured by the temperature measurement device 21 inserted through portal 22. The temperature increase, $\Delta T$, is computed by the microprocessor 23 by signals sent through lines 24 and 25. If the temperature increase, $\Delta T$, is not large enough (typically a few degrees centigrade), a signal is sent from the microprocessor 23 by line 26 to the microwave generator 19 to increase the energy output until a suitable temperature increase occurs. If $\Delta T$ is too large (typically about 50° C. or more), the energy output of the microwave generator 19 is decreased until $\Delta T$ is in an acceptable range. The energy level of the microwave generator 19 is stored in the microprocessor 23. The velocity of the fluid is measured by a flowmeter 27, and the measurement is sent by line 28 to the microprocessor 23.

Prior to field installation, the apparatus is calibrated using a known oil/water mixture. Preferably, the calibration is done with a recent sample from the wellhead, because the characteristics of water and oil at various well sites may vary affecting their heating by MWF. The calibration procedure will consist of characterizing the response of just the field water (brine) and just the field oil to the MWF, especially the amount of heating of each component as a function of the MWF intensity. Then a series of calibrations will be made at a number of fixed oil/water ratios of the mixture to characterize the response to the MWF. Then, as described below, the response characteristics will be reconciled with the theoretical prediction given below so that the microprocessor 23 can be programmed to give the correct oil/water cut from field measurements.

It will be necessary to have sets of calibration for those cases where additional components (such as gas or additives) will be present as a result of normal production activities. The microprocessor 23 will be programmed in such a manner that it can be instructed to make corrections for these additional components when required.

The microprocessor 23 is programmed to calculate the oil/water cut in accordance with the theory given below. This operation is based upon the information arriving via lines 24, 25, 26, and 28. A signal is then generated which indicates the oil/water cut. This signal is sent to an information center 29 by link 30. Link 30 may be a hardwire, a telemetry path, or another suitable method of transferring information. At the information center 29, the oil/water cut measurement is used as needed for proper production. Clearly, this information is of an instantaneous nature, which can be averaged as desired. This information may be recorded and/or stored in any number of ways.

Figure 2:
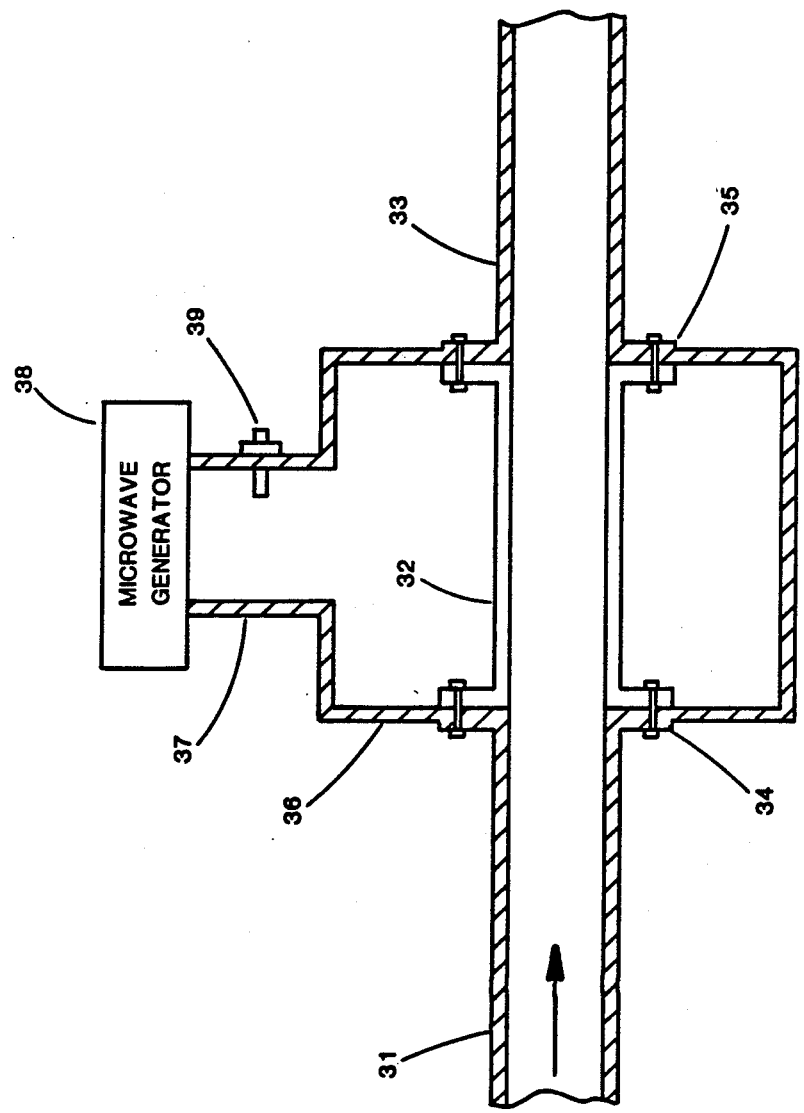
FIG. 2 is a diagrammatic view of an alternate embodiment of applicator for the MWF.

In FIG. 2, an alternate embodiment for the application of the microwave energy is shown. This would replace that part of the metal metering pipe section 12 of FIG. 1, consisting of parts 18, 19, and 20. The oil/water mixture flows through a metal pipe section 31 into a glass pipe section 32 and then out into a metal pipe section 33. The glass pipe section 32 is made of a glass or any other material that is transparent to the MWF and is attached to the metal pipe sections 31 and 33 by flanges 34 and 35. A metal box 36 encloses the glass pipe section 32. This metal box 36 has dimensions such that it acts as a multimode cavity with maximum MWF energy density in the location or the glass pipe section 32. The MWF is guided by waveguide 37 from a microwave generator 38. Tuning stub 39 is set to cause a maximum transfer of microwave energy from the microwave generator 38 to the multimode cavity 36. (Not illustrated in FIG. 2 are the other components of the apparatus, such as the mixing means, and temperature sensing means).

The two means of applying the microwave energy to the oil/water mixture shown in FIGS. 1 and 2 are not the only means, other means can be used. Other means than these specifically identified above can be used to mix the mixture, measure the temperature, etc.

Figure 3:
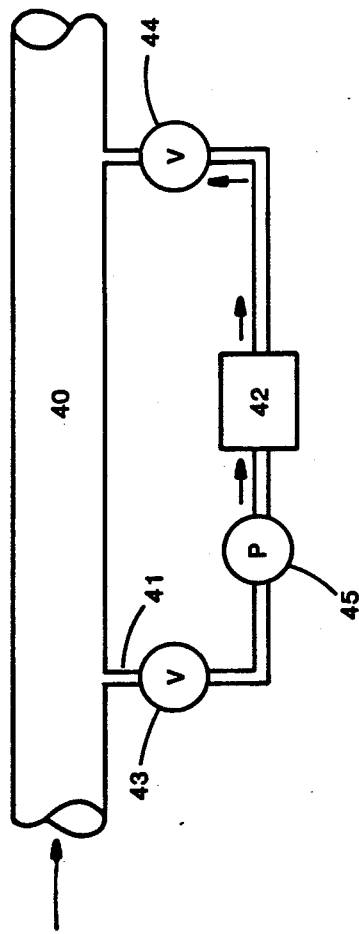
FIG. 3 is a diagrammatic view of an embodiment utilizing a bypass arrangement for the flow of liquids through the measurement equipment.

In certain circumstances, e.g., high volume flow rates, it may be advantageous to redirect a small portion of the total flow through the measuring apparatus. This can be done as shown in FIG. 3. A small bypass pipe 41 is connected to the main pipe 40 and returned to the main pipe 40 after passing through the oil/water cut measuring apparatus 42. The oil/water cut measuring apparatus 42 is as described above in FIG. 1 and 2. The flow of fluids through the bypass is controlled by valves 43 and 44 which may be controlled manually or remotely when a measurement is required. To ensure proper flow through the measuring apparatus 42, a pump 45 is operated whenever a measurement is being made. The pump serves the dual purpose of extracting the fluid from the main pipe and maintaining a constant velocity in the bypass conduit, thus ensuring an accurate measurement of temperature change. This information may be recorded and/or stored in any number of ways.

This invention is that when a mixture of oil and water is exposed to a MWF, the water, with its higher conductivity, will absorb more energy than the oil. Clearly, as is obvious to one skilled in the art, any mixture in which one component more readily absorbs more MWF energy than the other components can also be measured by the method of the present invention. From Poynting's theorem, one can show that a single component substance with dielectric constant $\epsilon'$ and loss tangent $\delta$ will absorb energy at the rate of $$P_v = (\text{watts/cm})^3 \quad (1)$$
$$= 0.556 f E_o^2 \epsilon' \tan \delta$$

where the frequency f of the electromagnetic field, the MWF, is in MHz and its electric field strength is $E_o$ (KV/cm). This absorbed energy will cause a temperature change of a single component (either oil or water) of density $\rho_i$ and specific heat capacity $C_{pi}$ is given by $$\frac{(dT)}{(dt)} = \frac{P_{vi}}{\rho_i C_{pi}} \quad (2)$$

or the temperature rise $\Delta T_i$ in a time $\Delta t$ is $$\Delta T_i = \frac{P_{vi} \Delta t}{\rho_i C_{pi}}, \quad (3)$$

where $\Delta t$ is the time the sample stays in the MWF. If there are two electrically different substances in a fluid mixture, then each will experience a temperature increase in proportion to its electrical thermochemical properties. Because of the intimate contact between the fluids, this will produce an average temperature rise of the mixture. On an average, then, a two-component system will experience a temperature rise given by $$<\Delta T> = \frac{m_o C_{po}}{<m><C_p>} \Delta T_o + \frac{m_w C_{pw}}{<m><C_p>} \Delta T_w$$

$$= \frac{(1)}{\left(1 + \frac{\alpha \rho_w}{(1-\alpha)\rho_o}\right)} \frac{(2)}{\left(1 + \frac{C_{pw}}{C_{po}}\right)} \Delta T_o + \quad (4)$$

$$\frac{(1)}{\left(1 + \frac{(1-\alpha)\rho_o}{\alpha \rho_w}\right)} \frac{(2)}{\left(1 + \frac{C_{po}}{C_{pw}}\right)} \Delta T_\omega$$

where
  $C_{po}$ = specific heat capacity of oil,
  $C_{pw}$ = specific heat capacity of water,
  $<C_p>$ = average specific heat capacity of mixture
  $m_o$ = mass of oil,
  $m_w$ = mass of water,
  $<m>$ = average mass of mixture,
  $\rho_o$ = mass density of oil,
  $\rho_w$ = mass density of water,
  $\alpha$ = fraction of mixture that is water,
  $\Delta T_o$ = temperature increase of oil component,
  $\Delta T_w$ = temperature increase of water component.

If the oil/water mixture is flowing through a pipe of radius r and length l with a volume flow rate v(cm$^3$/sec) then $$\Delta t = \frac{\pi r^2 l}{v}. \quad (5)$$

Then by combining equations (3), (4), and (5), an approximation of the functional relationship between the oil/water cut, $$\frac{(1-\alpha)}{\alpha},$$

is found. Thus for a mixture such as oil and water, accurate temperature increases can be obtained. For mixtures with more than two components, accurate temperature increases can be measured as long as the specific heat capacity ($C_p$) and the mass (m) or mass density (p) of the additional components are known, such as determined during the calibration process.

A series of tests showed that, for a typical mixture of crude oil and brine, the temperature increased as a function of exposure time. For a fixed exposure time, but with varying percentages of water, a very usable temperature increase was obtained and the same is true for a flowing mixture.

As the fraction of water, α, decreases, the temperature increase becomes so small, for a fixed MWF power level, as to be unusable. However, if the power level is increased at lower fractional water content, then a usable temperature increase results. This teaches us that the power level of the MWF must be adjusted in accordance with the fraction of water content. The simplest approach is to have the power level determined by the temperature differential.

The invention being thus described, it is obvious that said invention can be varied in many ways. Such variations are not to be regarded as a departure from the spirit and the scope of the invention; and, all such modifications as would be obvious to one skilled in the art are intended to be included within the scope of the following claims.

What is claimed is:

1. A method for measuring the ratio of components with different properties in a fluid mixture of those components flowing through a conduit comprising the steps of:
   (a) measuring the temperature of a fluid mixture in the conduit;
   (b) measuring the flow rate of the mixture in the conduit;
   (c) heating the fluid mixture by applying a microwave field to the mixture within the conduit;
   (d) measuring the temperature of the mixture in the conduit after it has been heated;
   (e) measuring the power input of the microwave field; and
   (f) determining the ratio of components present in the mixture.

2. The method of claim 1 wherein the heating of the fluid creates a sufficient temperature rise to allow measurement.

3. The method of claim 2 wherein the fluid is heated sufficiently to cause temperature rise of from about 2° C. to about 50° C.

4. A method for measuring the ratio of components present in a multi-component fluid comprising:
   (a) flowing a multi-component fluid through a conduit;
   (b) mixing the multi-component fluid to form a uniform mixture of the components in multi-component fluid;
   (c) measuring the temperature of the multi-component fluid prior to heating the fluid;
   (d) heating the multi-component fluid by applying microwave energy to the uniformly mixed fluid;
   (e) measuring the temperature of said uniformly mixed fluid after it has been heated;
   (f) measuring the power input of the microwave energy;
   (g) measuring the flow rate of the fluid within the conduit; and
   (h) determining the ratio of components in the fluid.

5. The method of claim 4 wherein the heating of the fluid creates a sufficient temperature rise to allow measurement.

6. The method of claim 5 wherein the fluid is heated sufficiently to cause temperature rise of from about 2° C. to about 50° C.

7. An apparatus for measuring the ratio of components present in a multi-component fluid comprising
   (a) a conduit passageway for flow of a multi-component liquid therethrough having an inlet and an outlet;
   (b) a first temperature measuring means for measuring the temperature of the multi-component liquid in the conduit, said first temperature measuring means located between the inlet of said conduit and before a means to apply microwave energy;
   (c) means to apply microwave energy to said multi-component liquid flowing in said conduit located downstream of said first temperature measuring means;
   (d) a second temperature measuring means for measuring the temperature of said multi-component fluid flowing in the conduit of said means to apply microwave energy;
   (e) a flow measuring means disposed along the conduct between said inlet and outlet for measuring the flow rate in the conduit; and
   (f) a means to calculate the ratio of components present from inputs received from said first temperature measuring means, said second temperature measuring means and said flow measuring means.

8. The apparatus of claim 7 wherein said means to apply microwave energy comprises a section of said conduit transparent to microwave energy and a microwave energy transmitter disposed over said transparent section.

9. The apparatus of claim 8 wherein said means to apply microwave energy comprises a section of said conduit transparent to microwave energy and a microwave energy transmitter disposed over said transparent section.

10. The apparatus of claim 7 further comprising a pump disposed between said inlet and said outlet of said conduit.

11. The apparatus of claim 7 wherein said measuring means are thermocouples.

12. The apparatus of claim 7 further comprising a means for controlling the output of said means for applying microwave energy which receives input from said temperature measuring means, said flow measuring means from which signals the amount of energy to be applied is determined and control signals are provided to said means for applying microwave energy.

13. The apparatus of claim 12 wherein said means to calculate and said means for controlling is a microprocessor.

14. The apparatus of claim 13 further comprising a pump disposed between said inlet and said outlet of said conduit.

15. The apparatus of claim 12 further comprising a pump disposed between said inlet and said outlet of said conduit.

16. An apparatus for measuring the rates of components present in a multi-component liquid flowing through a conduit comprising:
   (a) a conduit defining a passageway for flow of a multi-component liquid mixture therethrough having an inlet and outlet;
   (b) a first temperature measuring means for measuring the temperature of the multi-component liquid in the conduit, said first temperature measuring means located in the conduit between said inlet and a means to apply microwave energy;

(c) flow measuring means disposed within the conduit for measuring the flow rate in the conduit;

(d) mixing means within the conduit so as to produce a uniform mixture of the multi-component liquid;

(e) means to apply a microwave energy to the said uniformly mixed multi-component liquid within the conduit downstream of said first temperature measuring means to heat said multicomponent liquid;

(f) a second temperature measuring means for measuring the temperature of said liquid mixture in the conduit, said temperature measuring means located downstream of said means to apply microwave energy; and (g) a means to calculate the ratio of components present from inputs received from said first temperature measuring means, said second temperature measuring means and said flow measuring means.

17. The apparatus of claim 16 wherein said means to apply microwave energy comprises a section of said conduit transparent to microwave energy and a microwave energy transmitter disposed over said transparent section.

18. The apparatus of claim 17 wherein said means to apply microwave energy comprises a section of said conduit transparent to microwave energy and a microwave energy transmitter disposed over said transparent section.

19. The apparatus of claim 16 further comprising a pump disposed between said inlet and said outlet of said conduit.

20. The apparatus of claim 16 wherein said measuring means are thermocouples.

21. The apparatus of claim 16 wherein said mixing means is a plurality of plates disposed within said conduit.

22. The apparatus of claim 21 further comprising straightening vanes downstream of said mixing means.

23. The apparatus of claim 16 wherein said conduit is electrically insulating from the earth and from pipes connected to said inlet and outlet of said conduit.

24. The apparatus of claim 16 further comprising a means for controlling the output of said means for applying microwave energy which receives input from said temperature measuring means, said flow measuring means from which signals the amount of energy to be applied is determined and control signals are provided to said means for applying microwave energy.

25. The apparatus of claim 16 wherein said means to calculate and said means for controlling is a microprocessor.

* * * * *